United States Patent
Barrett et al.

(10) Patent No.: US 7,211,384 B2
(45) Date of Patent: May 1, 2007

(54) COMPARATIVE GENOMIC HYBRIDIZATION ASSAYS USING IMMOBILIZED OLIGONUCLEOTIDE TARGETS WITH INITIALLY SMALL SAMPLE SIZES AND COMPOSITIONS FOR PRACTICING THE SAME

(75) Inventors: Michael T. Barrett, Mountain View, CA (US); Alicia Scheffer, Redwood City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 277 days.

(21) Appl. No.: 10/448,298

(22) Filed: May 28, 2003

(65) Prior Publication Data

US 2004/0241658 A1 Dec. 2, 2004

(51) Int. Cl.
C12Q 1/68 (2006.01)
C12P 19/34 (2006.01)
C07H 19/00 (2006.01)
C07H 21/04 (2006.01)

(52) U.S. Cl. .................... 435/6; 435/91.2; 536/22.1; 536/24.31; 536/24.32; 536/24.33

(58) Field of Classification Search ............... 435/6, 435/91.2; 536/24.32, 24.33, 24.31, 22.1
See application file for complete search history.

(56) References Cited

U.S. PATENT DOCUMENTS

| | | | |
|---|---|---|---|
| 5,348,855 A | 9/1994 | Dattagupta et al. | |
| 5,447,841 A | 9/1995 | Gray et al. | |
| 5,665,549 A * | 9/1997 | Pinkel et al. ................. | 435/6 |
| 5,830,645 A * | 11/1998 | Pinkel et al. ................. | 435/6 |
| 5,965,362 A | 10/1999 | Pinkel et al. | |
| 6,335,167 B1 | 1/2000 | Pinkel et al. | |
| 6,159,685 A | 12/2000 | Pinkel et al. | |
| 6,197,501 B1 | 3/2001 | Cremer et al. | |
| 6,210,878 B1 | 4/2001 | Pinkel et al. | |
| 6,251,601 B1 | 6/2001 | Bao et al. | |
| 6,465,182 B1 | 10/2002 | Gray et al. | |
| 2002/0006622 A1 | 1/2002 | Bradley et al. | |

FOREIGN PATENT DOCUMENTS

WO WO 99/23256 5/1999
WO WO03/033724 A 4/2003

OTHER PUBLICATIONS

Dean et al. Comprehensive human genome amplification using multiple displacement amplification. PNAS, vol. 99, No. 8, pag 5261-5266, 2002.*
Lage et al. Whole genome analysis of genetic alterations in small DNA samples using hyperbranched strand displacement amplification and array-CGH. Genome res., vol. 13(2), Feb. 2003.*
Dean et al. Comprehensive human genome amplification using multiple displacement amplification. PNAS, vol. 99 (8), Apr. 2002.*

Dean et al., entitled "Comprehensive Human Genome Amplification Using Multiple Displacemetn Amplification," PNAS, Apr. 16, 2002, vol. 99, No. 8, pp. 5261-5266.

Hart et al., entitled "A GDP Dissociation Inhibitor That Serves as a GTPase Inhibitor for the Ras-Like Protein CDC42Hs," Science, vol. 258, Oct. 30, 1992, pp. 812-815.

Lage, et al., entitled "Whole Genome Analysis of Genetic Alterations in Small DNA Samples Using Hyperbranched Strand Displacement Amplification and Array—DGH," Genome Research, 13:294-307, 2003.

Pinkel et al., entitled "High Resolution Analysis of DNA Copy Number Variation Using Comparativ Genomic Hybridization to Microarrays," Nature Genetics, vol. 20, Oct. 1998, pp. 207-211.

Pollack et al., entitled "Genome-Wide Analysis of DNA Copy-Number Changes Using cDNA Microarrays," Nature Genetics, vol. 23, Sep. 1999, pp. 41-46.

Schena et al., entitled "Quantitative Monitoring of Gene Expression Patterns with a Complementary DNA Microarray," Science, vol. 270, Oct. 20, 1995, pp. 467-470.

Jose Lage, et al., "Whole Genome Analysis of Genetic Alterations in Small DNA Samples Using Hyper-branched strand displacement amplification and array-CGH"; Genome Research, Feb. 2003, vol. 13, No. 2, pp. 294-307.

Buckley, Patrick, G., et al., "A full-coverage, high-resolution human chromosome 22 genomic microarray for clinical and research applications."; Human Molecular Genetics, Dec. 1, 2002, vol. 11, No. 25, pp. 3221-3229.

Wang, Gang, et al., "Balanced-PCR Amplification allows unbiased identification of genomic copy changes in minute cell and tissue samples."; Nucleic Acids Research. May 2004, vol. 32, No. 9, May 2004, p. e76.

Hughes, S., et al.,; "Use of whole genome amplification and comparative genomic hybridization to detect chromosomal copy number alterations in cell line material and tumour tissue." Cytogenetic and Genome Research, 2004, vol. 105, No. 1, 2004, pp. 18-24.

(Continued)

Primary Examiner—Suryaprabha Chunduru

(57) ABSTRACT

Comparative genomic hybridization assays and compositions for use in practicing the same are provided. In the subject methods, at least first and second genomic templates are prepared from first and second genomic sources using an amplification reaction that employs a highly processive polymerase, where the amplification reaction produces amplification products having an average molecular size of at least about 10 kb with substantially no amplification bias. The resultant templates are then employed to produce at least first and second probe nucleic acid populations. The resultant probe nucleic acid populations are then contacted with a plurality of oligonucleotide target elements immobilized on a solid support surface and the binding of at least first and second populations is then evaluated. Also provided are kits for use in practicing the subject methods.

42 Claims, 4 Drawing Sheets

(4 of 4 Drawing Sheet(s) Filed in Color)

OTHER PUBLICATIONS

Pollack, J. R., et al., "Genome-wide Analysis of DNA Copy-number changes using cDNA microarrays", Nature Genetics, Nature America, New York, US, Vo. 23, No. 1, Sep. 1999, pp. 41-46.

Pinkel, D., et al., "High Resolution Analysis of DNA copy number variation using comparative genomic hybridization to microarrays", Nature Genetics, New York, NY, US vol. 20, Oct. 1998, pp. 207-211.

Solinas-Toldo, S, et al., "Matrix-Based Comparative Genomic Hybridization: Biochips to Screen for Genomic Imbalances"; Genese, Crhomosomes & Cancer, vol. 20, No. 4, 1997, pp. 399-407.

Albertson, Donna, G., Profiling breast cancer by array CGH.; Breast Cancer Research and Treatment, Apr. 2003; vol. 78, No. 3, Apr. 2003, pp. 289-298.

Cai W-W, et al.,; "Genome-Wide Detection of Chromosomal Imbalances in Tumors Using Bac Microarrays" Nature Biotechnology, Nature Publishing, US, vol. 20, No. 4, Apr. 2002, pp. 393-396.

Snijders, A. M., et al., "Assembly of Microarrays for Genome-Wide Measurement of DNA Copy Number" Nature Genetics, Nature America, New York, US, vol. 29, No. 3, Nov. 2001; pp. 263-264.

Bruder, C. E, et al., "High Resolution deletion analysis of constituional DNA from neurofibromatosis type 2 (NF2) patients using microarray-CGH."; Human Molecular Genetics; Feb. 1, 2001, vol. 10, No. 3, pp. 271-282.

Dean, Frank, B., et al.,; "Comprehensive Human Genome Amplification Using multiple displacement amplification.", Proceedings of the National Academy of Sciences of the United States of America, Apr. 16, 2002, vol. 99, No. 8, pp. 5261-5266.

Hosono, Seiyu, et al.,; Unbiased whole-genome amplification directly from clinical samples.; Genome Research., May 2003, vol. 13, No. 5, pp. 954-964.

Dean, F. B., et al., "Rapid amplification of plasmid and phage DNA using Phi29 DNA polymerase and multiply-primed rolling circle amplification", Genome Research, Cold Spring Harbor Laboratory Press, US, Vo. 11, No. 6, pp. 1095-1099.

* cited by examiner

20µg unamplified XY (red) vs 20µg unamplifed XX (green).

10ng amplified XY (red) vs 10ng amplifed XX (green).

20µg unamplified MDA-MB231 (red) vs 20µg unamplified XX (green)

20ng unamplified MDA-MB231 (red) vs 20µg unamplified XX (green)

ical field of the invention is comparative genomic hybridization (CGH).

COMPARATIVE GENOMIC HYBRIDIZATION ASSAYS USING IMMOBILIZED OLIGONUCLEOTIDE TARGETS WITH INITIALLY SMALL SAMPLE SIZES AND COMPOSITIONS FOR PRACTICING THE SAME

TECHNICAL FIELD

The technical field of the invention is comparative genomic hybridization (CGH).

BACKGROUND OF THE INVENTION

Many genomic and genetic studies are directed to the identification of differences in gene dosage or expression among cell populations for the study and detection of disease. For example, many malignancies involve the gain or loss of DNA sequences resulting in activation of oncogenes or inactivation of tumor suppressor genes. Identification of the genetic events leading to neoplastic transformation and subsequent progression can facilitate efforts to define the biological basis for disease, improve prognostication of therapeutic response, and permit earlier tumor detection. In addition, perinatal genetic problems frequently result from loss or gain of chromosome segments such as trisomy 21 or the micro deletion syndromes. Thus, methods of prenatal detection of such abnormalities can be helpful in early diagnosis of disease.

Comparative genomic hybridization (CGH) is one approach that has been employed to detect the presence and identify the location of amplified or deleted sequences. In one implementation of CGH, genomic DNA is isolated from normal reference cells, as well as from test cells (e.g., tumor cells). The two nucleic acids are differentially labeled and then simultaneously hybridized in situ to metaphase chromosomes of a reference cell. Chromosomal regions in the test cells which are at increased or decreased copy number can be identified by detecting regions where the ratio of signal from the two DNAs is altered. For example, those regions that have been decreased in copy number in the test cells will show relatively lower signal from the test DNA than the reference compared to other regions of the genome. Regions that have been increased in copy number in the test cells will show relatively higher signal from the test DNA.

In a recent variation of the above traditional CGH approach, the immobilized chromosome element has been replaced with a collection of solid support bound target nucleic acids, e.g., an array of BAC (bacterial artificial chromosome) clones or cDNAs. Such approaches offer benefits over immobilized chromosome approaches, including a higher resolution, as defined by the ability of the assay to localize chromosomal alterations to specific areas of the genome. However, these methods still have significant limitations in their ability to detect chromosomal alterations at single gene resolution (in the case of BAC clone arrays) or in non-coding regions of the genome in the case of cDNA clone arrays. In addition, array features containing longer lengths of nucleic acid sequence are more susceptible to binding cross-hybridizing sequences, where a given immobilized target nucleic acid hybridizes to more than one distinct probe sequence in solution. This property limits somewhat the ability of these technologies to detect low level amplifications and deletions sensitively and accurately.

Accordingly, there is interest in the development of improved array based CGH methods. Of particular interest would be the development of improved array based CGH methods in which small initial samples may be assayed.

Relevant Literature

Articles of interest include Dean et al., PNAS (Apr. 16, 2002) 99:5261–5266 and Lage et al., Genome Res (2003 February) 13(2):294–307. Also of interest are: U.S. Pat. Nos. 6,465,182; 6,335,167; 6,251,601; 6,210,878; 6,197,501; 6,159,685; 5,965,362; 5,830,645; 5,665,549; 5,447,841 and 5,348,855, as well as U.S. Application Ser. No. 2002/0006622 and published PCT application WO 99/23256. Articles of interest include: Science (1992); 258:818–21; Nat. Genet. (1998) 20:207–11; Nat. Genet. (1999)23:41–6; and Science (1995) 270: 467–470.

SUMMARY OF THE INVENTION

Comparative genomic hybridization assays and compositions for use in practicing the same are provided. In the subject methods, at least first and second genomic templates are prepared from first and second genomic sources using an amplification reaction that employs a highly processive polymerase, where the amplification reaction produces amplification products having an average molecular size of at least about 10 kb with substantially no amplification bias. The resultant templates are then employed to produce at least first and second probe nucleic acid populations. The resultant probe nucleic acid populations are then contacted with a plurality of oligonucleotide target elements immobilized on a solid support surface and the binding of at least first and second populations is then evaluated. Also provided are kits for use in practicing the subject methods.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DEFINITIONS

Figure 1A:
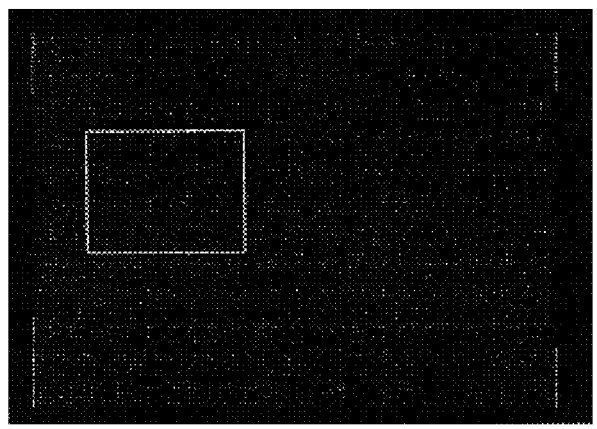
FIGS. 1A and 1B. Agilent Human microarrays hybridized using protocols with starting material of A) 20 µg, and B) 10 ng of genomic DNA from XY (red) a XX (green). Top panel complete array image: Bottom panel section of the array containing three Y-specific genes (arrows) that hybridize with DNA from male samples (red).
Figure 1A:
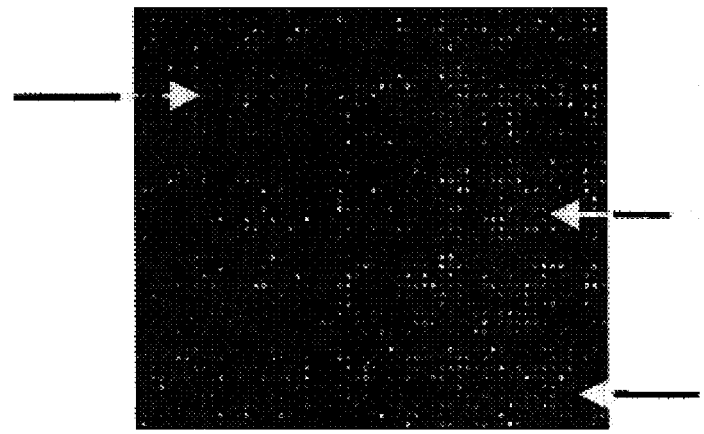
Figure 1B:
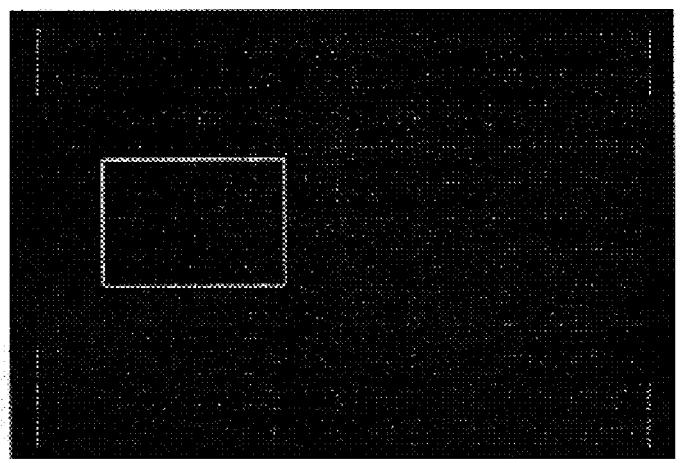
Figure 1B:
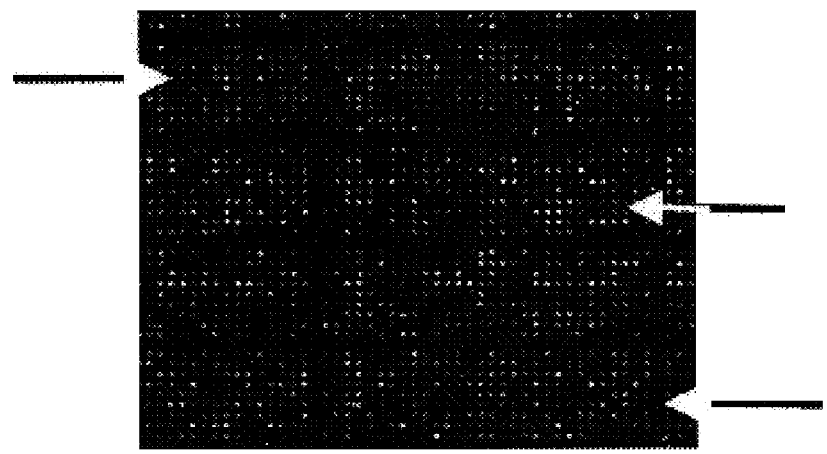

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" as used herein denotes single stranded nucleotide multimers of from about 10 to 100 nucleotides and up to 200 nucleotides in length.

The term "oligomer" is used herein to indicate a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other nucleic acids which are C-glycosides of a purine or pyrimidine base, polypeptides (proteins), polysaccharides (starches, or polysugars), and other chemical entities that contain repeating units of like chemical structure.

The term "sample" as used herein relates to a material or mixture of materials, typically, although not necessarily, in fluid form, containing one or more components of interest.

The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The phrase "oligonucleotide target element bound to a surface of a solid support" refers to an oligonucleotide or mimetic thereof, e.g., PNA, that is immobilized on a surface of a solid substrate, where the substrate can have a variety of configurations, e.g., a sheet, bead, or other structure. In certain embodiments, the collections of oligonucleotide target elements employed herein are present on a surface of the same planar support, e.g., in the form of an array.

The term "array" encompasses the term "microarray" and refers to an ordered array presented for binding to nucleic acids and the like.

An "array," includes any two-dimensional or substantially two-dimensional (as well as a three-dimensional) arrangement of addressable regions bearing nucleic acids, particularly oligonucleotides or synthetic mimetics thereof, and the like. Where the arrays are arrays of nucleic acids, the nucleic acids may be adsorbed, physisorbed, chemisorbed, or covalently attached to the arrays at any point or points along the nucleic acid chain.

Any given substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than 20 cm$^2$ or even less than 10 cm$^2$, e.g., less than about 5 cm$^2$, including less than about 1 cm$^2$, less than about 1 mm$^2$, e.g., 100 µ$^2$, or even smaller. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, 20%, 50%, 95%, 99% or 100% of the total number of features). Inter-feature areas will typically (but not essentially) be present which do not carry any nucleic acids (or other biopolymer or chemical moiety of a type of which the features are composed). Such inter-feature areas typically will be present where the arrays are formed by processes involving drop deposition of reagents but may not be present when, for example, light directed array fabrication processes are used. It will be appreciated though, that the inter-feature areas, when present, could be of various sizes and configurations.

Each array may cover an area of less than 200 cm$^2$, or even less than 50 cm$^2$, 5 cm$^2$, 1 cm$^2$, 0.5 cm$^2$, or 0.1 cm$^2$. In certain embodiments, the substrate carrying the one or more arrays will be shaped generally as a rectangular solid (although other shapes are possible), having a length of more than 4 mm and less than 150 mm, usually more than 4 mm and less than 80 mm, more usually less than 20 mm; a width of more than 4 mm and less than 150 mm, usually less than 80 mm and more usually less than 20 mm; and a thickness of more than 0.01 mm and less than 5.0 mm, usually more than 0.1 mm and less than 2 mm and more usually more than 0.2 and less than 1.5 mm, such as more than about 0.8 mm and less than about 1.2 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse-jets of either nucleic acid precursor units (such as monomers) in the case of in situ fabrication, or the previously obtained nucleic acid. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat No. 6,323,043 U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, light directed array fabrication methods may be used. Inter-feature areas need not be present.

An array is "addressable" when it has multiple regions of different moieties (e.g., different oligonucleotide sequences) such that a region (i.e., a "feature" or "spot" of the array) at a particular predetermined location (i.e., an "address") on the array will detect a particular probe sequence. Array features are typically, but need not be, separated by intervening spaces. In the case of an array in the context of the present application, the "probe" will be referenced in certain embodiments as a moiety in a mobile phase (typically fluid), to be detected by "targets" which are bound to the substrate at the various regions.

A "scan region" refers to a contiguous (preferably, rectangular) area in which the array spots or features of interest, as defined above, are found or detected. Where fluorescent labels are employed, the scan region is that portion of the total area illuminated from which the resulting fluorescence is detected and recorded. Where other detection protocols are employed, the scan region is that portion of the total area queried from which resulting signal is detected and recorded. For the purposes of this invention and with respect to fluorescent detection embodiments, the scan region includes the entire area of the slide scanned in each pass of the lens, between the first feature of is interest, and the last feature of interest, even if there exist intervening areas that lack features of interest.

An "array layout" refers to one or more characteristics of the features, such as feature positioning on the substrate, one or more feature dimensions, and an indication of a moiety at a given location. "Hybridizing" and "binding", with respect to nucleic acids, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

The term "stringent assay conditions" as used herein refers to conditions that are compatible to produce binding pairs of probes and targets of sufficient complementarity to provide for the desired level of specificity in the assay while being incompatible to the formation of binding pairs between binding members of insufficient complementary to provide for the desired specificity. An example of stringent assay conditions is rotating hybridization at 65° C. in a salt based hybridization buffer with a total monovalent cation concentration of 1.5M (e.g., as described in U.S. patent application Ser. No. 09/655,482 filed on Sep. 5, 2000, the disclosure of which is herein incorporated by reference) followed by washes of 0.5×SSC and 0.1×SSC at room temperature. Stringent assay conditions are hybridization conditions that are at least as stringent as the above representative conditions, where a given set of conditions are considered to be at least as stringent if substantially no additional binding complexes that lack sufficient complementarity to provide for the desired specificity are produced in the given set of conditions as compared to the above specific conditions, where by "substantially no more" is meant less than about 5-fold more, typically less than about 3-fold more. Other stringent hybridization conditions are known in the art and may also be employed, as appropriate.

DESCRIPTION OF THE SPECIFIC EMBODIMENTS

Comparative genomic hybridization assays and compositions for use in practicing the same are provided. In the subject methods, at least first and second genomic templates are prepared from first and second genomic sources using an amplification reaction that employs a highly processive polymerase, where the amplification reaction produces amplification products having an average molecular size of at least about 10 kb with substantially no amplification bias. The resultant templates are then employed to produce at least first and second probe nucleic acid populations. The resultant probe nucleic acid populations are then contacted with a plurality of oligonucleotide target elements immobilized on a solid support surface and the binding of at least first and second populations is then evaluated. Also provided are kits for use in practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components that are described in the publications that might be used in connection with the presently described invention.

As summarized above, the present invention provides methods for comparing populations of probe nucleic acids and compositions for use therein, where the invention is particular suited for use with small initial sample amounts. In further describing the present invention, the subject methods are discussed first in greater detail, followed by a review of representative kits for use in practicing the subject methods.

Methods

The subject invention provides methods for comparing populations of probe nucleic acids and compositions for use therein, where a feature of the subject methods is the use of genomic templates prepared from initial genomic sources using an amplification reaction that produces amplification products having an average molecular size of at least about 10 kb with substantially no amplification bias.

In practicing the subject methods, the first step is to provide at least two different populations or collections of probe nucleic acids from two or more genomic templates which are prepared as described above. The two or more populations of probe nucleic acids may or may not be labeled, depending on the particular detection protocol employed in a given assay. For example, in certain embodiments, binding events on the surface of a substrate may be detected by means other than by detection of a labeled probe nucleic acids, such as by change in conformation of a conformationally labeled immobilized target, detection of electrical signals caused by binding events on the substrate surface, etc. In many embodiments, however, the populations of probe nucleic acids are labeled, where the populations may be labeled with the same label or different labels, depending on the actual assay protocol employed. For example, where each population is to be contacted with different but identical arrays, each probe nucleic acid population or collection may be labeled with the same label. Alternatively, where both populations are to be simultaneously contacted with a single array of targets, i.e., cohybridized to the same array of immobilized target nucleic acids, the populations are generally distinguishably or differentially labeled with respect to each other.

The two or more (i.e., at least first and second, where the number of different collections may, in certain embodiments, be three, four or more) populations of probe nucleic acids are prepared from different genomic templates that are, in turn, prepared from different genomic sources.

As such, the first step in many embodiments of the subject methods is to prepare a genomic template from an initial genomic source for each genome that is to be compared. The next step in many embodiments of the subject methods is to then prepare a collection of probe nucleic acids, e.g., labeled probe nucleic acids, from the prepared genomic template for each genome that is to be compared. Each of these initial steps is now described separately in greater detail.

The term genome refers to all nucleic acid sequences (coding and non-coding) and elements present in any virus, single cell (prokaryote and eukaryote) or each cell type in a metazoan organism. The term genome also applies to any naturally occurring or induced variation of these sequences that may be present in a mutant or disease variant of any virus or cell type. These sequences include, but are not limited to, those involved in the maintenance, replication, segregation, and higher order structures (e.g. folding and compaction of DNA in chromatin and chromosomes), or other functions, if any, of the nucleic acids as well as all the coding regions and their corresponding regulatory elements needed to produce and maintain each particle, cell or cell type in a given organism.

For example, the human genome consists of approximately $3.0 \times 10^9$ base pairs of DNA organized into distinct chromosomes. The genome of a normal diploid somatic human cell consists of 22 pairs of autosomes (chromosomes 1 to 22) and either chromosomes X and Y (males) or a pair of chromosome Xs (female) for a total of 46 chromosomes. A genome of a cancer cell may contain variable numbers of each chromosome in addition to deletions, rearrangements and amplification of any subchromosomal region or DNA sequence.

By "genomic source" is meant the initial nucleic acids that are used as the original nucleic acid source from which the probe nucleic acids are produced, e.g., as a template in the labeled probe nucleic acid generation protocols described in greater detail below.

The genomic source may be prepared using any convenient protocol. In many embodiments, the genomic source is prepared by first obtaining a starting composition of genomic DNA, e.g., a nuclear fraction of a cell lysate, where any convenient means for obtaining such a fraction may be employed and numerous protocols for doing so are well known in the art. The genomic source is, in many embodiments of interest, genomic DNA representing the entire genome from a particular organism, tissue or cell type.

A given initial genomic source may be prepared from a subject, for example a plant or an animal, that is suspected of being homozygous or heterozygous for a deletion or amplification of a genomic region. In certain embodiments, the average size of the constituent molecules that make up the initial genomic source typically have an average size of at least about 1 Mb, where a representative range of sizes is from about 50 to about 250 Mb or more, while in other embodiments, the sizes may not exceed about 1 MB, such that the may be about 1 Mb or smaller, e.g., less than about 500 Kb, etc.

Following obtainment of the initial genomic source, the initial genomic source is amplified to produce a genomic template from the initial genomic source. As summarized above, each initial genomic source is amplified in an amplification reaction that produces amplification products having an average molecular size of at least about 10 kb with substantially no amplification bias.

By average molecular size of at least about 10 kb is meant that the amplification products produced by the amplification reaction have an average molecular size of at least about 10 kb, where the size range of the products may vary from about 100 bp to about 100 Mb, such as from about 1 kb to about 1 Mb, but the average size of all of the products produced by many embodiments ranges from about 1 kb to about 1 Mb, such as from about 10 kb to about 100 kb. By substantially no amplification bias is meant that the any amplification bias present among any two or more regions, e.g., chromosomal loci, of the initial genomic source does not exceed about 3-fold, and in certain embodiments does not exceed about 2-fold or 1-fold, where amplification bias is determined using the protocol described in Dean et al., PNAS (2002) 99:5261–5266.

A feature of the subject amplification protocol is that it provides the above described amplification product from an initially small amount of genomic source nucleic acid. As such, the amount of "input" genomic source nucleic acid that is employed in the subject protocols may, in certain embodiments, be less than about 10 ng, such as less than about 5 µg, such that in many embodiments the input amount ranges from about 10 ng to about 1 µg, usually from about 10 ng to about 500 ng. The amplification protocol employed is further characterized by producing a much greater amount of genomic template from the small amount of input genomic source, where the amount of amplification product produced by the subject methods is typically at least about 1 µg, such as at least about 10 µg, and may range from about 1 µg to about 500 µg, such as from about 5 µg to about 50 µg.

In many embodiments, the amplification protocol is one that employs a highly processive polymerase. By highly processive polymerase is meant a polymerase that elongates a DNA chain without dissociation over extended lengths of nucleic acid, where extended lengths means at least about 50 nt long, such as at least about 100 nt long or longer, including at least about 250 nt long or longer, at least about 500 nt long or longer, at least about 1000 nt long or longer.

In many embodiments, the polymerase employed in the amplification step is a phage polymerase. Of interest in certain embodiments is the use of a φ29-type DNA polymerase. By φ29-type DNA polymerase is meant either: (i) that phage polymerase in cells infected with a φ29-type phage; (ii) a φ29-type DNA polymerase chosen from the DNA polymerases of phages φ29, Cp-1, PRD1, φ15, φ21, PZE, PZA, Nf, M2Y, B103, SF5, GA-1, Cp-5, Cp-7, PR4, PR5, PR722, and L17; or (iii) a φ29-type polymerase modified to have less than ten percent of the exonuclease activity of the naturally-occurring polymerase, e.g., less than one percent, including substantially no, exonuclease activity. Representative φ29 type polymerases of interest include, but are not limited to, those polymerases described in U.S. Pat. No. 5,198,543, the disclosure of which is herein incorporated by reference.

In certain embodiments, the amplification protocol is one that employs a collection of exonuclease resistant random oligomer primers. The random oligomer primers generally range in length from about 3 to 10, usually from about 4 to 8 nt, where in many embodiments the oligomer primers are pentamers, hexamers or septamers. By exonuclease resistant is meant a primer that has been modified so that it is not subject to exonuclease activity of the polymerase, where specific modifications of interest include, but are not limited to: one or more 5' terminal nitroindole residues, etc.

The polymerase, genomic source and primer reagents, as described above, are combined with one or more additional reagents, e.g., buffers, sources of monovalent and divalent cations, etc., to produce a reaction mixture. The resultant reaction mixture is then subjected to amplification conditions sufficient to produce the desired amplification product, i.e., genomic template, as described above.

In certain embodiments, the amplification protocol employed is an isothermal strand displacement protocol. By isothermal is meant that the protocol does not employ thermal cycling.

Amplification is typically carried out a temperature ranging from about 5° C. to about 40° C., usually from about 15° C. to about 30° C., for a period of time ranging from about 1 hr to about 72 hr, usually from about 5 hr to about 12 hr, following which time the amplification reaction is stopped, e.g., by inactivating the polymerase, such as by heating the amplification reaction mixture to a temperature of about 50° C. to about 100° C. for a period of time ranging from about 1 min to about 10 min.

Of particular interest in certain embodiments is amplification of the initial genomic source using a multiple displacement amplification (MDA) protocol, such as that described in Dean et al., PNAS (2002) 99:5261–5266.

The above step of amplifying each initial genomic source results in the production of a genomic template for each initial genomic source. Where desired, the genomic template may be fragmented in the probe generation protocol, as desired, to produce a fragmented genomic template, where the molecules have a desired average size range, e.g., up to about 10 Kb, such as up to about 1 Kb, where fragmentation may be achieved using any convenient protocol, including but not limited to: mechanical protocols, e.g., sonication, shearing, etc., chemical protocols, e.g., enzyme digestion, etc.

Following provision of the genomic template, and any initial processing steps (e.g., fragmentation, etc.) as described above, the collection of probe nucleic acids is prepared from the genomic template for use in the subject methods. In certain embodiments of particular interest, the collection of probe nucleic acids prepared from the initial genomic source is one that has substantially the same complexity as the complexity of the initial genomic source and genomic template. In other words, the prepared collection of probe nucleic acids is a "non-reduced-complexity" collection of probe nucleic acids, as compared to the initial genomic source, genomic template and genome of the organism from which the initial genomic source is obtained. A non-reduced complexity collection is one that is not produced in a manner designed to reduce the complexity of the sample, e.g., is not produced using collections of primers that are designed to prime only a certain percentage or fraction of the initial genomic source. For example, a reduced complexity collection of probe nucleic acids is one that has been produced by a protocol that only amplifies a certain portion, fraction or region of the genomic source used to prepare the collection.

In certain embodiments, non-reduced complexity collections of probe nucleic acids are ones in which substantially all, if not all, of the sequences found in the initial genomic source (and organism genome from which the initial source is obtained) are present in the produced probe population. By substantially all is meant typically at least about 75%, such as at least about 80%, at least about 85%, at least about 90% or more, including at least about 95%, at least about 95% etc, of the total genomic sequences are present in the produced probe population, where the above percentage values are number of bases in the produced probe population as compared to the total number of bases in the genomic source. Because substantially all, if not all, of the sequences found in the genomic source are present in the produced population of probe nucleic acids, the resultant population of probe nucleic acids is not one that is reduced in complexity with respect to the initial genomic template, i.e., it is not a reduced complexity population of probe nucleic acids.

A non-reduced complexity collection of probe nucleic acids can be readily identified using a number of different protocols. One convenient protocol for determining whether a given collection of probe nucleic acids is a non-reduced complexity collection of probe nucleic acids is to screen the collection using a genome wide array of target nucleic acids for the genomic source of interest. Thus, one can tell whether a given collection of probe nucleic acids has non-reduced complexity with respect to its genomic source by assaying the collection with a genomic wide array for the genomic source. The genomic wide array of the genomic source is an array of target nucleic acids in which the entire genomic source is screened at a sufficiently high resolution, where the resolution is typically at least about 1 Mb, e.g., at least about 500 Kb, such as at least about 250 Kb; including at least about 100 Kb, e.g., 50 Kb or higher (such as 25 Kb, 15 Kb, 10 Kb or higher), where resolution in this context means lengths of the genomic source between regions present on the array in the form of immobilized targets. In such a genomic wide assay of sample, a non-reduced complexity sample is one in which substantially all of the array features on the array provide a positive signal, where by substantially all is meant at least about 50%, such as at least about 60, 70, 75, 80, 85, 90 or 95% (by number) or more.

In many embodiments of interest, the collection or population of probe nucleic acids that is prepared in this step of the subject methods is one that is labeled with a detectable label. In the embodiments where the population of probe nucleic acids is a non-reduced complexity population of nucleic acids, as described above, the labeled probe nucleic acids are prepared in a manner that does not reduce the complexity to any significant extent as compared to the initial genomic source. A number of different nucleic acid labeling protocols are known in the art and may be employed to produce a population of labeled probe nucleic acids. The particular protocol may include the use of labeled primers, labeled nucleotides, modified nucleotides that can be conjugated with different dyes, one or more amplification steps, etc.

In one type of representative labeling protocol of interest, the genomic template, which most often is fragmented (as described above), is employed in the preparation of labeled probe nucleic acids as a genomic template from which the labeled probe nucleic acids are enzymatically produced. Different types of template dependent labeled nucleic acid generation protocols are known in the art. In certain types of protocols, the template is employed in a non-amplifying primer extension nucleic acid generation protocol. In yet other embodiments, the template is employed in an amplifying primer extension protocol.

Of interest in the embodiments described above, whether they be amplifying or non-amplifying primer extension reactions, is the use of a set of primers that results in the production of the desired probe nucleic acid collection of high complexity, i.e., comparable or substantially similar complexity to the initial genomic source. In many embodiments, the above described population of probe nucleic acids in which substantially all, if not all, of the sequences found in the initial genomic source are present, is produced using a primer mixture of random primers, i.e., primers of random sequence. The primers employed in the subject methods may vary in length, and in many embodiments range in length from about 3 to about 25 nt, sometimes from about 5 to about 20 nt and sometimes from about 5 to about 10 nt. The total number of random primers of different sequence that is present in a given population of random primers may vary, and depends on the length of the primers in the set. As such, in the sets of random primers, which include all possible variations, the total number of primers n in the set of primers that is employed is $4^Y$, where Y is the length of the primers. Thus, where the primer set is made up of 3-mers, Y=3 and the total number n of random primers in the set is $4^3$ or 64. Likewise, where the primer set is made up of 8-mers, Y=8 and the total number n of random primers in the set is $4^8$ or 65,536. Typically, an excess of random primers is employed, such that in a given primer set employed in the subject invention, multiple copies of each different random primer sequence is present, and the total number of primer molecules in the set far exceeds the total number of distinct primer sequences, where the total number may range from about $1.0 \times 10^{10}$ to about $1.0 \times 10^{20}$ such as from about $1.0 \times 10^{13}$ to about $1.0 \times 10^{17}$, e.g., $3.7 \times 10^{15}$. The primers described above and throughout this specification may be prepared using any suitable method, such as, for example, the known phosphotriester and phosphite triester methods, or automated embodiments thereof. In one such automated embodiment, dialkyl phosphoramidites are used as starting materials and may be synthesized as described by Beaucage et al. (1981), Tetrahedron Letters 22, 1859. One method for synthesizing oligonucleotides on a modified solid support is described in U.S. Pat. No. 4,458,066.

As indicated above, in generating labeled probe nucleic acids according to these embodiments of subject methods, the above-described genomic template and random primer population are employed together in a primer extension reaction that produces the desired labeled probe nucleic acids. Primer extension reactions for generating labeled nucleic acids are well known to those of skill in the art, and any convenient protocol may be employed, so long as the above described genomic source (being used as a template) and population of random primers are employed. In this step of the subject methods, the primer is contacted with the template under conditions sufficient to extend the primer and produce a primer extension product, either in an amplifying or in a non-amplifying manner (where a non-amplifying manner is one in which essentially a single product is produced per template strand). As such, the above primers are contacted with the genomic template in the presence of a sufficient DNA polymerase under primer extension conditions sufficient to produce the desired primer extension molecules. DNA polymerases of interest include, but are not limited to, polymerases derived from *E. coli*, thermophilic bacteria, archaebacteria, phage, yeasts, *Neurosporas, Drosophilas*, primates and rodents. The DNA polymerase extends the primer according to the genomic template to which it is hybridized in the presence of additional reagents which may include, but are not limited to: dNTPs; monovalent and divalent cations, e.g. KCl, $MgCl_2$; sulfhydryl reagents, e.g. dithiothreitol; and buffering agents, e.g. Tris-Cl.

Extension products that are produced as described above are typically labeled in the present methods. As such, the reagents employed in the subject primer extension reactions typically include a labeling reagent, where the labeling reagent may be the primer or a labeled nucleotide, which may be labeled with a directly or indirectly detectable label. A directly detectable label is one that can be directly detected without the use of additional reagents, while an indirectly detectable label is one that is detectable by employing one or more additional reagents, e.g., where the label is a member of a signal producing system made up of two or more components. In many embodiments, the label is a directly detectable label, such as a fluorescent label, where the labeling reagent employed in such embodiments is a fluorescently tagged nucleotide(s), e.g., dCTP. Fluorescent moieties which may be used to tag nucleotides for producing labeled probe nucleic acids include, but are not limited to: fluorescein, the cyanine dyes, such as Cy3, Cy5, Alexa 555, Bodipy 630/650, and the like. Other labels may also be employed as are known in the art.

In the primer extension reactions employed in the subject methods of these embodiments, the genomic template is typically first subjected to strand disassociation condition, e.g., subjected to a temperature ranging from about 80° C. to about 100° C., usually from about 90° C. to about 95° C. for a period of time, and the resultant disassociated template molecules are then contacted with the primer molecules under annealing conditions, where the temperature of the template and primer composition is reduced to an annealing temperature of from about 20° C. to about 80° C., usually from about 37° C. to about 65° C. In certain embodiments, a "snap-cooling" protocol is employed, where the temperature is reduced to the annealing temperature, or to about 4° C. or below in a period of from about 1 s to about 30 s, usually from about 5 s to about 10 s.

The resultant annealed primer/template hybrids are then maintained in a reaction mixture that includes the above-discussed reagents at a sufficient temperature and for a sufficient period of time to produce the desired labeled probe nucleic acids. Typically, this incubation temperature ranges from about 20° C. to about 75° C., usually from about 37° C. to about 65° C. The incubation time typically ranges from about 5 min to about 18 hr, usually from about 1 hr to about 12 hr.

In yet other embodiments, the collection of probe nucleic acids may be one that is of reduced complexity as compared to the initial genomic source. By reduced complexity is meant that the complexity of the produced collection of probe nucleic acids is at least about 20-fold less, such as at least about 25-fold less, at least about 50-fold less, at least about 75-fold less, at least about 90-fold less, at least about 95-fold less, than the complexity of the initial genomic source, in terms of total numbers of sequences found in the produced population of probes as compared to the initial source, up to and including a single gene locus being represented in the collection. The reduced complexity can be achieved in a number of different manners, such as by using gene specific primers in the generation labeled probe nucleic acids, by reducing the complexity of the genomic source used to prepare the probe nucleic acids, etc. As with the above non-reduced-complexity protocols, in these reduced complexity protocols, the probe nucleic acids prepared in many embodiments are labeled probe nucleic acids. Any convenient labeling protocol, such as the above described representative protocols, may be employed, where the protocols are adapted to provide for the desired reduced complexity, e.g., by using gene specific instead of random primers.

Using the above protocols, at least a first collection of probe nucleic acids and a second collection of probe nucleic acids are produced from two different genomic templates, e.g., a reference and test genomic template, from two different genomic sources. As indicated above, depending on the particular assay protocol (e.g., whether both populations are to be hybridized simultaneously to a single array or whether each population is to be hybridized to two different but substantially identical, if not identical, arrays) the populations may be labeled with the same or different labels. As such, a feature of certain embodiments is that the different collections or populations of produced labeled probe nucleic acids are all labeled with the same label, such that they are not distinguishably labeled. In yet other embodiments, a feature of the different collections or populations of produced labeled probe nucleic acids is that the first and second labels are typically distinguishable from each other. The constituent probe members of the above produced collections typically range in length from about 100 to about 10,000 nt, such as from about 200 to about 10,000 nt, including from about 100 to 1,000 nt, from about 100 to about 500, etc.

In the next step of the subject methods, the collections or populations of labeled probe nucleic acids produced by the subject methods are contacted to a plurality of target elements under conditions such that nucleic acid hybridization to the target elements can occur. The probe collections can be contacted to the target elements either simultaneously or serially. In many embodiments the probe compositions are contacted with the plurality of target elements, e.g., the array of targets, simultaneously. Depending on how the collections or populations are labeled, the collections or populations may be contacted with the same array or different arrays, where when the collections or populations are contacted with different arrays, the different arrays are substantially, if not completely, identical to each other in terms of target feature content and organization.

A feature of the present invention is that the substrate immobilized target nucleic acids are oligonucleotide target nucleic acids. By oligonucleotide is meant a nucleic acid having a length ranging from about 10 to about 200 including from about 10 or about 20 to about 100 nt, where in many embodiments the target nucleic acids range in length from about 50 to about 90 nt or about 50 to about 80 nt, such as from about 50 to about 70 nt.

Target nucleic acids employed in such applications can be derived from virtually any source. Typically, the targets will be nucleic acid molecules having sequences derived from representative locations along a chromosome of interest, a chromosomal region of interest, an entire genome of interest, a cDNA library, and the like.

The choice of target nucleic acids to use may be influenced by prior knowledge of the association of a particular chromosome or chromosomal region with certain disease conditions. International Application WO 93/18186 provides a list of chromosomal abnormalities and associated diseases, which are described in the scientific literature. Alternatively, whole genome screening to identify new regions subject to frequent changes in copy number can be performed using the methods of the present invention. In these embodiments, target elements usually contain nucleic acids representative of locations distributed over the entire genome. In such embodiments, the resolution may vary, where in many embodiments of interest, the resolution is at least about 500 Kb, such as at least about 250 Kb, at least about 200 Kb, at least about 150 Kb, at least about 100 Kb, at least about 50 Kb, including at least about 25 Kb, at least about 10 Kb or higher. By resolution is meant the spacing on the genome between sequences found in the targets. In some embodiments (e.g., using a large number of target elements of high complexity) all sequences in the genome can be present in the array. The spacing between different locations of the genome that are represented in the targets of the collection of targets may also vary, and may be uniform, such that the spacing is substantially the same, if not the same, between sampled regions, or non-uniform, as desired.

In some embodiments, previously identified regions from a particular chromosomal region of interest are used as targets. Such regions are becoming available as a result of rapid progress of the worldwide initiative in genomics. In certain embodiments, the array can include targets which "tile" a particular region (which have been identified in a previous assay), by which is meant that the targets correspond to region of interest as well as genomic sequences found at defined intervals on either side, i.e., 5' and 3' of, the region of interest, where the intervals may or may not be uniform, and may be tailored with respect to the particular region of interest and the assay objective. In other words, the tiling density may be tailored based on the particular region of interest and the assay objective. Such "tiled" arrays and assays employing the same are useful in a number of applications, including applications where one identifies a region of interest at a first resolution, and then uses tiled arrays tailored to the initially identified region to further assay the region at a higher resolution, e.g., in an iterative protocol.

Of interest are both coding and non-coding genomic regions, where by coding region is meant a region of one or more exons that is transcribed into an mRNA product and from there translated into a protein produce, while by non-coding region is meant any sequences outside of the exon regions, where such regions may include regulatory sequences, e.g., promoters, enhancers, introns, etc. In certain embodiments, one can have at least some of the targets directed to non-coding regions and others directed to coding regions. In certain embodiments, one can have all of the targets directed to non-coding sequences. In certain embodiments, one can have all of the targets directed to coding sequences.

The oligonucleotide targets employed in the subject methods are immobilized on a solid support. Many methods for immobilizing nucleic acids on a variety of solid support surfaces are known in the art. For instance, the solid support may be a membrane, glass, plastic, or a bead. The desired component may be covalently bound or noncovalently attached through nonspecific binding, adsorption, physisorption or chemisorption. The immobilization of nucleic acids on solid support surfaces is discussed more fully below.

A wide variety of organic and inorganic polymers, as well as other materials, both natural and synthetic, may be employed as the material for the solid surface. Illustrative solid surfaces include nitrocellulose, nylon, glass, fused silica, diazotized membranes (paper or nylon), silicones, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface will usually include appropriate functionalities to provide for the covalent attachment. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces are well known and is amply illustrated in the literature. For example, methods for immobilizing nucleic acids by introduction of various functional groups to the molecules is known (see, e.g., Bischoff et al., Anal. Biochem. 164:336–344 (1987); Kremsky et al., Nuc. Acids Res. 15:2891–2910 (1987)). Modified nucleotides can be placed on the target using PCR primers containing the modified nucleotide, or by enzymatic end labeling with modified nucleotides, or by non-enzymatic synthetic methods Use of membrane supports (e.g., nitrocellulose, nylon, polypropylene) for the nucleic acid arrays of the invention is advantageous in certain embodiments because of well-developed technology employing manual and robotic methods of arraying targets at relatively high element densities (e.g., up to 30–40/cm.sup.2). In addition, such membranes are generally available and protocols and equipment for hybridization to membranes is well known. Many membrane materials, however, have considerable fluorescence emission, where fluorescent labels are used to detect hybridization.

To optimize a given assay format one of skill can determine sensitivity of fluorescence detection for different combinations of membrane type, fluorochrome, excitation and emission bands, spot size and the like. In addition, low fluorescence background membranes have been described (see, e.g., Chu et al., Electrophoresis 13:105–114 (1992)).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorochrome and membranes can thus be determined. Serial dilutions of pairs of fluorochrome in known relative proportions can also be analyzed to determine the accuracy with which fluorescence ratio measurements reflect actual fluorochrome ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from the about 1 mm diameter down to about 1 µm can be used with these materials. Small array members containing small amounts of concentrated target DNA are conveniently used for high complexity comparative hybridizations since the total amount of probe available for binding to each element will be limited. Thus it may be advantageous in certain embodiments to have small array members that contain a small amount of concentrated target DNA so that the signal that is obtained is highly localized and bright. Such small array members are typically used in arrays with densities greater than $10^4/cm^2$. Relatively simple approaches capable of quantitative fluorescent imaging of 1 $cm^2$ areas have been described that permit acquisition of data from a large number of members in a single image (see, e.g., Wittrup et. al. Cytometry 16:206–213 (1994)).

Covalent attachment of the target nucleic acids to glass or synthetic fused silica can be accomplished according to a number of known techniques. Such substrates provide a very low fluorescence substrate, and a highly efficient hybridization environment.

There are many possible approaches to coupling nucleic acids to glass that employ commercially available reagents. For instance, materials for preparation of silanized glass with a number of functional groups are commercially available or can be prepared using standard techniques. Alternatively, quartz cover slips, which have at least 10-fold lower auto fluorescence than glass, can be silanized. In certain embodiments of interest, silanization of the surface is accomplished using the protocols described in U.S. Pat. No. 6,444,268, the disclosure of which is herein incorporated by reference, where the resultant surfaces have low surface energy that results from the use of a mixture of passive and functionalized silanization moieties to modify the glass surface, i.e., they have low surface energy silanized surfaces. Additional linking protocols of interest include, but are not limited to: polylysine as well as those disclosed in U.S. Pat. No. 6,319,674, the disclosure of which is herein incorporated by reference. The targets can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith et al. Science, 258:1122–1126 (1992)). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In the subject methods (as summarized above), the copy number of particular nucleic acid sequences in two probe collections are compared by hybridizing the probes to one or more target nucleic acid arrays, as described above. The hybridization signal intensity, and the ratio of intensities, produced by the probes on each of the target elements is determined. Since signal intensities on a target element can be influenced by factors other than the copy number of a probe in solution, for certain embodiments an analysis is conducted where two labeled populations are present with distinct labels. Thus comparison of the signal intensities for a specific target element permits a direct comparison of copy number for a given sequence. Different target elements will reflect the copy numbers for different sequences in the probe populations The comparison can reveal situations where each sample includes a certain number of copies of a sequence of interest, but the numbers of copies in each sample are different. The comparison can also reveal situations where one sample is devoid of any copies of the sequence of interest, and the other sample includes one or more copies of the sequence of interest.

Standard hybridization techniques (using high stringency hybridization conditions) are used to probe a target nucleic acid array. Suitable methods are described in references describing CGH techniques (Kallioniemi et al., Science 258:818–821 (1992) and WO 93/18186). Several guides to general techniques are available, e.g., Tijssen, Hybridization with Nucleic Acid Probes, Parts I and II (Elsevier, Amsterdam 1993). For a descriptions of techniques suitable for in situ hybridizations see, Gall et al. Meth. Enzymol., 21:470–480 (1981) and Angerer et al. in Genetic Engineering: Principles and Methods Setlow and Hollaender, Eds. Vol 7, pgs 43–65 (plenum Press, New York 1985). See also U.S. Pat. Nos. 6,335,167; 6,197,501; 5,830,645; and 5,665,549; the disclosures of which are herein incorporate by reference.

Generally, nucleic acid hybridizations comprise the following major steps: (1) immobilization of target nucleic acids; (2) pre-hybridization treatment to increase accessibility of target DNA, and to reduce nonspecific binding; (3) hybridization of the mixture of nucleic acids to the nucleic acid on the solid surface, typically under high stringency conditions; (4) post-hybridization washes to remove nucleic acid fragments not bound in the hybridization and (5) detection of the hybridized nucleic acid fragments. The reagents used in each of these steps and their conditions for use vary depending on the particular application.

As indicated above, hybridization is carried out under suitable hybridization conditions, which may vary in stringency as desired. In certain embodiments, highly stringent hybridization conditions may be employed. The term "high stringent hybridization conditions" as used herein refers to conditions that are compatible to produce nucleic acid binding complexes on an array surface between complementary binding members, i.e., between immobilized targets and complementary probes in a sample. Representative high stringency assay conditions that may be employed in these embodiments are provided above.

The above hybridization step may include agitation of the immobilized targets and the sample of probe nucleic acids, where the agitation may be accomplished using any convenient protocol, e.g., shaking, rotating, spinning, and the like.

Following hybridization, the surface of immobilized targets is typically washed to remove unbound probe nucleic acids. Washing may be performed using any convenient washing protocol, where the washing conditions are typically stringent, as described above.

Following hybridization and washing, as described above, the hybridization of the labeled nucleic acids to the targets is then detected using standard techniques so that the surface of immobilized targets, e.g., array, is read. Reading of the resultant hybridized array may be accomplished by illuminating the array and reading the location and intensity of resulting fluorescence at each feature of the array to detect any binding complexes on the surface of the array. For example, a scanner may be used for this purpose which is similar to the AGILENT MICROARRAY SCANNER available from Agilent Technologies, Palo Alto, Calif. Other suitable devices and methods are described in U.S. patent application Ser. No. 09/846,125 "Reading Multi-Featured Arrays" by Dorsel et al.; and U.S. Pat. No. 6,406,849, which references are incorporated herein by reference. However, arrays may be read by any other method or apparatus than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). In the case of indirect labeling, subsequent treatment of the array with the appropriate reagents may be employed to enable reading of the array. Some methods of detection, such as surface plasmon resonance, do not require any labeling of the probe nucleic acids, and are suitable for some embodiments.

Results from the reading or evaluating may be raw results (such as fluorescence intensity readings for each feature in one or more color channels) or may be processed results, such as obtained by subtracting a background measurement, or by rejecting a reading for a feature which is below a predetermined threshold and/or forming conclusions based on the pattern read from the array (such as whether or not a particular target sequence may have been present in the sample, or whether or not a pattern indicates a particular condition of an organism from which the sample came).

In certain embodiments, the subject methods include a step of transmitting data or results from at least one of the detecting and deriving steps, also referred to herein as evaluating, as described above, to a remote location. By "remote location" is meant a location other than the location at which the array is present and hybridization occur. For example, a remote location could be another location (e.g. office, lab, etc.) in the same city, another location in a different city, another location in a different state, another location in a different country, etc. As such, when one item is indicated as being "remote" from another, what is meant is that the two items are at least in different buildings, and may be at least one mile, ten miles, or at least one hundred miles apart.

"Communicating" information means transmitting the data representing that information as electrical-signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. The data may be transmitted to the remote location for further evaluation and/or use. Any convenient telecommunications means may be employed for transmitting the data, e.g., facsimile, modem, internet, etc.

A feature of the above methods is that they are sufficiently sensitive to detect a single copy number difference or change in the amount of a sequence of interest between any two given samples. In other words, the subject methods are capable of detecting a single copy number variation in a sequence between any two samples. As such, the subject methods are highly sensitive methods of comparing the copy numbers of one or more sequences between two or more samples.

Utility

The above-described methods find use in any application in which one wishes to compare the copy number of nucleic acid sequences found in two or more populations. One type of representative application in which the subject methods find use is the quantitative comparison of copy number of one nucleic acid sequence in a first collection of nucleic acid molecules relative to the copy number of the same sequence in a second collection.

As such, the present invention may be used in methods of comparing abnormal nucleic acid copy number and mapping of chromosomal abnormalities associated with disease. In many embodiments, the subject methods are employed in applications that use target nucleic acids immobilized on a solid support, to which differentially labeled probe nucleic acids produced as described above are hybridized. Analysis of processed results of the described hybridization experiments provides information about the relative copy number of nucleic acid domains, e.g. genes, in genomes.

Such applications compare the copy numbers of sequences capable of binding to the target elements. Variations in copy number detectable by the methods of the invention may arise in different ways. For example, copy number may be altered as a result of amplification or deletion of a chromosomal region, e.g. as commonly occurs in cancer. Representative applications in which the subject methods find use are further described in U.S. Pat. Nos. 6,335,167; 6,197,501; 5,830,645; and 5,665,549; the disclosures of which are herein incorporated by reference.

The subject methods find particular use in high resolution CGH applications where initially small sample volumes are to be analyzed, such as the small sample volumes described above. Small samples may be derived after purification of subpopulations of cells of interest from a starting tissue sample. For example, single and multi-parameter flow cytometry can identify small numbers of abnormal cells in a background of large numbers of normal cells in a biopsy or mixed cell population. Another technique that may be used to produce small samples of purified cells is laser capture microdissection.

Kits

Also provided are kits for use in the subject invention, where such kits may comprise containers, each with one or more of the various reagents/compositions utilized in the methods, where such reagents/compositions typically at least include a collection of immobilized oligonucleotide targets, e.g., one or more arrays of oligonucleotide targets, and reagents employed in genomic template and/or labeled probe production, e.g., a highly processive polymerase, exonuclease resistant primers, random primers, buffers, the appropriate nucleotide triphosphates (e.g. dATP, dCTP, dGTP, dTTP), DNA polymerase, labeling reagents, e.g., labeled nucleotides, and the like. Where the kits are specifically designed for use in CGH applications, the kits may further include labeling reagents for making two or more collections of distinguishably labeled nucleic acids according to the subject methods, an array of target nucleic acids, hybridization solution, etc.

Finally, the kits may further include instructions for using the kit components in the subject methods. The instructions may be printed on a substrate, such as paper or plastic, etc. As such, the instructions may be present in the kits as a package-insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc.

The following examples are offered by way of illustration and not by way of limitation.

EXPERIMENTAL

Figure 2A:
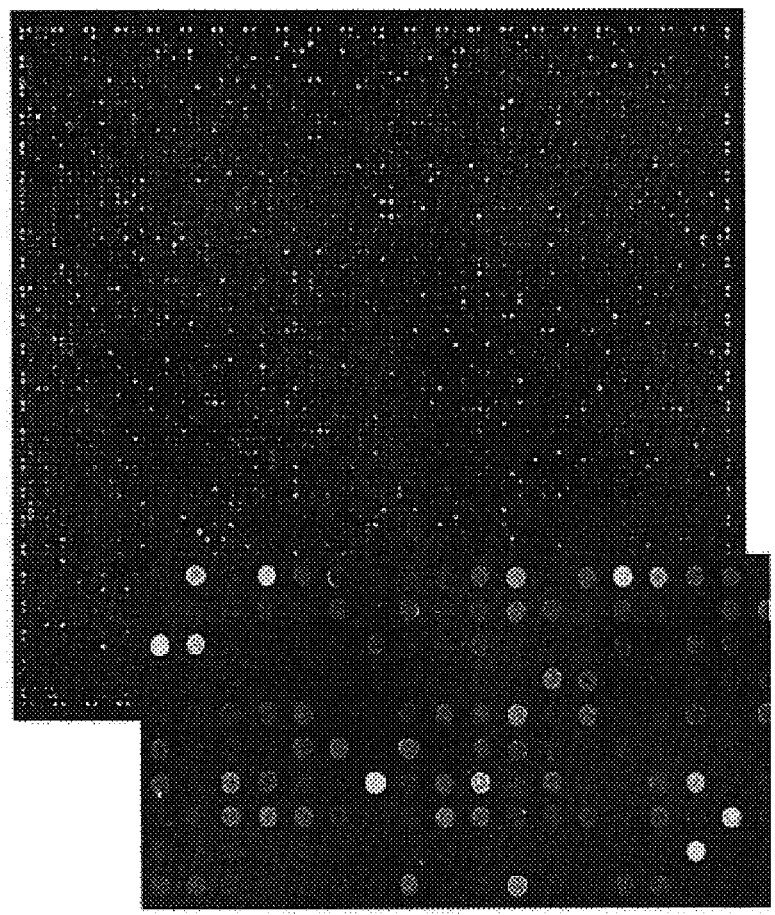
FIGS. 2A and 2B. Agilent Human microarrays hybridized using protocols with starting material of A) 20 µg, and B) 20 ng of genomic DNA from MDA-MB-231 breast cancer cells (red) using 20 µg of genomic DNA from XX (green) in each experiment.
Figure 2B:
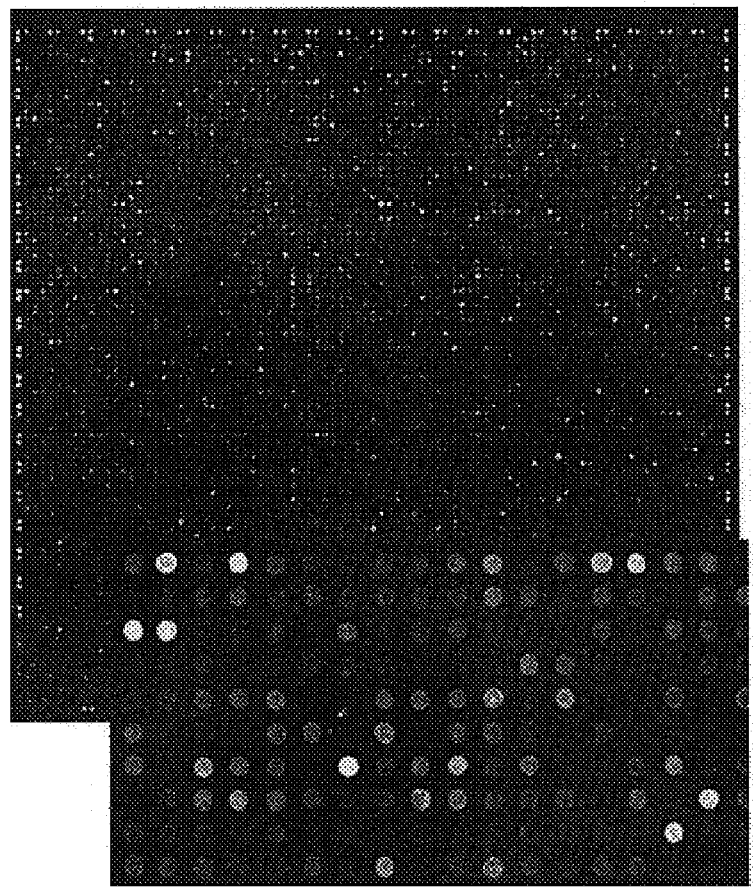

In the following experiment, the highly processive DNA polymerase φ29 is employed to linearly amplify as little as <10 ng of genomic DNA to produce sufficient high quality DNA template suitable for comprehensive high resolution microarray experiments. The following experiments show that the quality of the template generated with this polymerase is suitable for high-resolution CGH experiments (FIGS. 1 and 2).

Genomic male and female DNAs were amplified using φ29 MDA reagents obtained from the Molecular Staging Repli-G-2500S kit (New Haven Conn.) for 16 hrs @ 30° C. according to the supplier's instructions. Following this step, the reaction was halted by inactivating the polymerase at 65° C. for 3 minutes. After quantification, 20 µg of MDA DNA was used, without prior purification, as template in CGH labeling reactions. In another experiment genomic DNA from breast cancer cells (MDA-MB-231) were amplified using φ29 MDA reagents. In each experiment samples were digested with 25 units each of appropriate restriction enzymes (e.g. RsaI and AluI [Promega, Madison Wis.]) for two hours at 37° C. Digested samples were purified with the Qiagen (Valencia, Calif.) Qiaquick PCR Cleanup kit. Cy3- or Cy5-dUTPs were incorporated into digested, purified female or male DNA respectively using the BioPrime labeling kit (Invitrogen, Carlsbad, Calif.). Briefly, 6 µg digested genomic DNA was denatured in the presence of random octamers, then incubated with 3 nmol Cy-labeled dUTP, unlabeled dNTPs and Klenow fragment for 2 hrs at 37° C. The labeling reaction was purified with Centricon YM-30 columns (Millipore Corp, Bedford, Mass.). (Cy3 and Cy5 samples were pooled, denatured and reannealed in the presence of 50 ug Cot-1 DNA, 20 µg yeast tRNA (Invitrogen, Carlsbad, Calif.) and 2.5 ul×Agilent oligonucleotide microarray control target (Operon, Hayward, Calif.). Samples were then mixed with 2× Agilent deposition array buffer and hybridized to Human Catalogue arrays under coverslip overnight ar 65° C. Hybridizations consisted of the following combinations of DNA: a) non-amplified male and non-amplified female, b) amplified male and amplified female, c) non-amplified MDA-MB231 and non-amplifed female, d) amplified MDA-MB-231 and non-amplifed female. Arrays were subsequently washed in buffer 1 (0.5× SSC, 0.001% Triton X-100) for 5 minutes at room temperature, then transferred to and washed in buffer 2 (0.1×SSC, 0.001% Triton X-100) for another 5 minutes at room temperature. The arrays were scanned on an Agilent microarray scanner and analyzed with Agilent feature extraction software.

Another experimental design consists of preparing a suspension of single from a sample of interest. The cells or nuclei from this suspension are stained with a DNA-specific dye, such as propidium iodide, DAPI or Hoechst 33258. Cells are then passed in front of an illumination source such as a laser, and the dyes are fluorescently activated by light of the appropriate wavelength. Cell populations are then resolved and sorted according to their DNA content (ploidy) including hypodiploid (<2N) diploid (2N), aneuploid, and tetraploid (4N) cells. The genomic DNA from these sorted samples are extracted using standard techniques, then used in the same amplification, labeling and hybridization protocols described above. Other sorting strategies include DNA dyes in combinations with various antibodies to identify and sort cell populations of interest.

It is evident from the above results and discussion that this invention describes the development of protocols for preparing whole genome samples from small amounts of starting materials that can detect the copy numbers of any region in a given genome and their application to CGH assays using immobilized oligonucleotide targets and composition. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for comparing the copy number of at least one nucleic acid sequence in at least two genomic sources, said method comprising:
   (a) preparing at least a first genomic template from a first genomic source and a second genomic template from a second genomic source, wherein each of said first and second templates are prepared by amplifying each of said first and second genomic sources in an amplification reaction wit a highly processive polymerase that produces amplification products having an average molecular size of at least about 10 kb with substantially no amplification bias;
   (b) preparing at least a first collection of nucleic acid probe molecules from said first template and a second collection of nucleic acid probe molecules from said second template;
   (c) contacting said first and second collections of nucleic acid probe molecules with one or more pluralites of oligonucleotide target elements bound to a surface of a solid support, each target element comprising a target nucleic acid; and
   (d) evaluating the binding of the first and second collections of nucleic acid probe molecules to the same target nucleic acid to compare the copy number of at least one nucleic acid sequence in said at least two genomic sources.

2. The method according to claim 1, wherein said target nucleic acids range in size from about 20 nt to about 200 nt in length.

3. The method according to claim 2, wherein said target nucleic acids range in size from about 20 to about 100 nt in length.

4. The method according to claim 3, wherein said target nucleic acids range in size from about 50 to about 80 nt in length.

5. The method according to claim 1, wherein said probe nucleic acids range in length from about 100 to about 10000 nt in length.

6. The method according to claim 1, wherein said highly processive polymerase of said amplification reaction is a φ29-type polymerase.

7. The method according to claim 6, wherein said φ29-type polymerase is φ29 polymerase.

8. The method according to claim 1, wherein said amplification reaction has an amplification bias that is less than about 3-fold for any given two or more loci of said genomic sources.

9. The method according to claim 1, wherein said amplification reaction is an isothermal strand displacement amplification reaction.

10. The method according to claim 1, wherein said amplification reaction employs a population of random exonuclease resistant oligomer primers.

11. The method according to claim 10, wherein said primers are hexamers.

12. The method according to claim 1, wherein each of said collections of probe nucleic acids is prepared by a primer extension reaction using said genomic templates.

13. The method according to claim 1, wherein said contacting occurs under stringent hybridization conditions.

14. The method according to claim 1 wherein said collections of probe nucleic acids are contacted with a single array of target nucleic acids.

15. The method according to 14, wherein said collections of probe nucleic acids are distinguishably labeled.

16. The method according to claim 1, wherein each collection of probe nucleic acids is separately contacted with a plurality of target nucleic acids.

17. The method according to claim 1, wherein said plurality of oligonucleotide target elements comprises oligonucleotide target elements that are complementary to non-coding genomic regions.

18. The method according to claim 1, wherein said plurality of oligonucleotide target elements comprises oligonucleotide target elements that are complementary to coding genomic regions.

19. The method according to claim 1, wherein the solid support is a plurality of beads.

20. The method according to claim 1, wherein the solid support is a planar substrate.

21. The method according to claim 1, wherein said planar substrate is glass.

22. The method according to claim 21, wherein said glass planar substrate comprises a low surface energy silanized surface.

23. The method according to claim 21, wherein said planar substrate is plastic.

24. The method of claim 1, wherein said plurality of target elements bound to a solid surface comprise an array.

25. The method according to claim 1, wherein said method is capable of detecting a one copy deletion between said first and second collections of probe nucleic acids.

26. The method according to claim 1, wherein said method further comprises a data transmission step in which a result from said evaluating is transmitted from a first location to a second location.

27. The method according to claim 26, wherein said second location is a remote location.

28. A method comprising receiving data representing a result of said reading obtained by the method of claim 1.

29. A method for comparing the copy number of at least one nucleic acid sequence in at least two genomic sources, said method comprising:
   (a) preparing at least a first genomic template from a first genomic source and a second genomic template from a second genomic source, wherein each of said first and second templates are prepared by amplifying each of said first and second genomic sources in an amplification reaction with a highly processive polymerase that produces amplification products having an average molecular size of at least about 10 kb with substantially no amplification bias;

(b) preparing at least a first collection of nucleic acid probe molecules from said first genomic template and a second collection of nucleic acid probe molecules from said second genomic template, wherein each of said first and second collections are prepared by using a set of random primers with a genomic template produced according to step (a) in a primer extension reaction;

(c) contacting said first and second collections of nucleic acid probe molecules with one or more pluralities of oligonucleotide target elements bound to a surface of a solid support, each target element comprising a target nucleic acid; and (d) evaluating the binding of the first and second collections of nucleic acid probe molecules to the same target nucleic acid to compare the copy number of at least one nucleic acid sequence in said at least two genomic sources.

30. The method according to claim 29, wherein said set of primers is made up of primers having a length Y and the total number of different primer sequences present in said set is $4^Y$.

31. The method according to claim 30, wherein Y ranges from 3 to 25.

32. The method according to claim 29, wherein said target nucleic acids range in size from about 10 nt to about 200 nt in length.

33. The method according to claim 29, wherein each of said collections of probe nucleic acids is labeled.

34. The method according to claim 29, wherein said contacting occurs under stringent hybridization conditions.

35. The method according to claim 29, wherein the collections of probe nucleic acids are contacted with a single array of target nucleic acids.

36. The method according to claim 35, wherein said collections of probe nucleic acids are distinguishably labeled.

37. The method according to claim 29, wherein each collection of probe nucleic acids is separately contacted wit a plurality of target nucleic acids.

38. The method according to claim 29, wherein said plurality of oligonucleotide target elements bound to a surface of a solid support includes sequences representative of locations distributed across at least a portion of a genome.

39. The method according to claim 34, wherein said locations have a uniform spacing.

40. The method according to claim 34, wherein said locations have a non-uniform spacing.

41. The method according to claim 29, wherein said plurality of oligonucleotide target elements bound to a surface of a solid support samples a genome at a resolution of at least about 250 Kb.

42. The method of claim 29, wherein said method is capable of detecting a one copy deletion between said first and second collections of probe nucleic acids.

* * * * *